(12) United States Patent
Panitch

(10) Patent No.: US 9,034,815 B2
(45) Date of Patent: May 19, 2015

(54) POLYPEPTIDE FOR TREATING OR PREVENTING ADHESIONS

(75) Inventor: Alyssa Panitch, W. Lafayette, IN (US)

(73) Assignee: Moerae Matrix, Inc, Morristown, NJ (US)

( * ) Notice: Subject to any disclaimer, the term of this patent is extended or adjusted under 35 U.S.C. 154(b) by 835 days.

(21) Appl. No.: 12/582,516

(22) Filed: Oct. 20, 2009

(65) Prior Publication Data

US 2010/0098760 A1 Apr. 22, 2010
US 2013/0101671 A9 Apr. 25, 2013

Related U.S. Application Data

(63) Continuation-in-part of application No. 11/972,459, filed on Jan. 10, 2008, now Pat. No. 8,536,303.

(60) Provisional application No. 61/106,834, filed on Oct. 20, 2008, provisional application No. 60/880,137, filed on Jan. 10, 2007.

(51) Int. Cl.
*A61K 38/16* (2006.01)
*C07K 14/00* (2006.01)

(52) U.S. Cl.
CPC ................. *A61K 38/16* (2013.01); *C07K 14/00* (2013.01)

(58) Field of Classification Search
CPC ............................. C07K 14/00; A61K 38/16
See application file for complete search history.

(56) References Cited

U.S. PATENT DOCUMENTS

| | | | |
|---|---|---|---|
| 4,105,027 A | 8/1978 | Lundquist | |
| 4,192,309 A | 3/1980 | Poulsen | |
| 4,227,522 A | 10/1980 | Carris | |
| 4,627,432 A | 12/1986 | Newell et al. | |
| 4,778,054 A | 10/1988 | Newell et al. | |
| 4,811,731 A | 3/1989 | Newell et al. | |
| 5,035,237 A | 7/1991 | Newell et al. | |
| 5,565,350 A | 10/1996 | Kmiec | |
| 6,921,527 B2 | 7/2005 | Platz et al. | |
| 7,767,642 B2 * | 8/2010 | Schroeder ................... | 424/1.69 |
| 2003/0190364 A1 | 10/2003 | Panitch et al. | |
| 2006/0293234 A1 * | 12/2006 | Schroeder ...................... | 514/12 |
| 2008/0293640 A1 * | 11/2008 | Brophy et al. ................. | 514/14 |

FOREIGN PATENT DOCUMENTS

| WO | 91/16038 | | 10/1991 | | |
|---|---|---|---|---|---|
| WO | 93/22443 | | 11/1993 | | |
| WO | WO 2006/071456 | * | 7/2006 | ............. | A61K 38/17 |
| WO | WO 2008/085191 | * | 7/2008 | ............. | A61K 38/10 |

OTHER PUBLICATIONS

Morrison et al., 2001, Combinatorial alanine-scanning, Current Opinion in Chemical Biology, 5: 302-307.*

Del Gaizo et al., 2003, A Novel TAT-Mitochondrial Signal Sequence Fusion Protein Is Processed, Stays in Mitochondria, and Crosses the Placenta, Molecular Therapy, 7(6): 720-730.*
Ho et al., 2001, Synthetic Protein Transduction Domains: Enhanced Transduction Potential in Vitro and in Vivo, Cancer Res, 61: 474-477.*
Hayess et al., 1997, Effect of Protein Kinase Inhibitors on Activity of Mammalian Small Heat-Shock Protein (HSP25) Kinase, Biochemical Pharmacology, 53: 1239-1247.*
Schneider et al., 1998, In Vivo Evaluation of hsp27 as an Inhibitor of Actin Polymerization: Hsp27 Limits Actin Stress Fiber and Focal Adhesion Formation After Heat Shock, Journal of Cellular Physiology, 177: 575-584.*
Gerthoffer et al., 2001, Invited Review: Focal adhesion and small heat shock proteins in the regulation of actin remodeling and contractility in smooth muscle, J Appl Physiol, 91: 963-972.*
Beck et al., 2000, Molecular chaperones in the kidney: distribution, putative roles, and regulation, Am J Physiol Renal Physiol, 279: 203-215.*
Keezer et al., Angiogenesis Inhibitors Target the Endothelial Cell Cytoskeleton through Altered Regulation of Heat Shock Protein 27 and Cofilin, Cancer Res, 63: 6405-6412.*
Dalle-Donne et al., 2001, The Actin Cytoskeleton Response to oxidants: From Small Heat Shock Protein Phosphorylation to Changes in the Redox State of Actin Itself, Free Radical Biology & Medicine, 31(12): 1624-1632.*
de Graauw et al., 2005, Heat Shock Protein 27 is the Major Differentially Phosphorylated Protein Involved in Renal Epithelial Cellular Stress Response and Controls Focal Adhesion Organization and Apoptosis, J Biol Chem, 280: 29885-29898.*
Jobanputra, S. and Wexner, SD, "Systemic guide to complex cases from adhesive disease," Colorectal Dis., 9 Suppl 2: 54-59, 2007.
Weibel, M.A. and Majno, G., "Peritoneal adhesion and their relation to abdominal surgery," Am. J. Surg., 126: 345-353, 1973.
Merrifield, R. B. et al., "Solid Phase Peptide Synthesis. I. Synthesis of a Tetrapeptide," J. Am. Chem. Soc. 85: 2149-2154, 1963.
Carpino, L. A. and Han, G. Y., "9-Fluorenylmethoxycarbonyl amino-protecting group," J. Org. Chem., 37(22): 3403-3409, 1972.
Fields, G. B. and Noble, R. L., "Solid phase peptide synthesis utilizing 9-fluorenylmethoxycarbonyl amino acids," Int. J. Pept. Protein Res. 35: 161-214, 1990.
Smith, T. F. and Waterman, M. S., "Comparison of biosequences," Adv. Appl. Math. 2:482-489, 1981.

(Continued)

*Primary Examiner* — Amber D Steele
(74) *Attorney, Agent, or Firm* — Beverly W. Lubit

(57) ABSTRACT

The described invention provides compositions and methods for treating or preventing adhesions in a subject in need thereof, the method comprising the step of (a) administering an adhesion-reducing amount of a composition comprising a polypeptide having the amino acid sequence YARAAAR-QARAKALARQLGVAA [SEQ ID NO: 1] or a functional equivalent thereof and a carrier. The methods are clinically useful for reducing formation of adhesions initially and for therapeutic treatment of existing scars.

32 Claims, No Drawings

(56) References Cited

OTHER PUBLICATIONS

Needleman, S. B. and Wunsch, C. D., "A General Method Applicable to the Search for Similarities in the Amino Acid Sequence of Two Proteins," J. Mol. Biol. 48: 443-453, 1970.
Pearson, W. R. and Lipman, D. J., "Improved tolls for biological sequence comparison," Proc. Natl. Acad. Sci. 85: 2444-2448, 1988.
Higgins, D. G. and Sharp, P. M., "CLUSTAL: a package for performing multiple sequence alignment on a microcomputer," Gene, 73: 237-244, 1988.
Higgins D. G. and Sharp, P. M., "Fast and sensitive multiple sequence alignments on a microcomputer," Comput Appl Biosci, 5 (2): 151-153, 1989.
Corpet, F., "Multiple sequence alignment with hierarchical clustering," Nucleic Acids Research, 16(22):10881-10890, 1988.
Huang, X. et al., "Parallelization of a local similarity algorithm," Computer Applications in the Biosciences, 8(2): 155-165, 1992.
Pearson, W. R., "Using the FASTA Program to Search Protein and DNA Sequence Databases," Methods in Molecular Biology, 24: 307-331, 1994.
Altschul, S. F. et al., "Gapped BLAST and PSI-BLAST: a new generation of protein database search programs," Nucleic Acids Res. 25:3389-3402, 1997.
Henikoff, S. and Henikoff, J. G., "Amino acid substitution matrices from protein blocks," Proc. Natl. Acad. Sci. USA, 89:10915-10919, 1989.
Karline, S. and Altschul, S. F., "Applications and statistics for multiple high-scoring segments in molecular sequences," Proc. Natl. Acad. Sci. USA 90:5873-5787, 1993.
Wooten, J. C. and Federhen, S., "Statistics of local complexity in amino-acid-sequences and sequence databases," Comput. Chem., 17:149-163, 1993.
Claverie, J. M. and States, D. J., "Information enhancement methods for large scale sequence analysis," Comput. Chem., 17:191-201, 1993.
Meyers, E. W. and Miller, W., "Optimal alignments in linear space," Computer Appli Biosci. 4(1): 11-17, 1988.
Seal, B. L. and Panitch, A., "Physical polymer matrices based on affinity interactions between peptides and polysaccharides," Biomacromolecules, 4:1572-1582, 2003.
Peterson, T. A. et al., "Design, Development, Manufacturing, and Testing of Transdermal Drug Delivery Systems," in Transdermal and Topical Drug Delivery Systems, Ed. Ghosh, T.K. et al., pp. 249-297, Interpharm Press, IL, 1997.
Graham, F. L. and Prevec, L., "Manipulation of Adenovirus Vectors," in Gene Transfer and Expression Protocols, Ed. Murray, E. J., pp. 109-128, The Humana Press Inc., Clifton, NJ, 1991.
Buckenmaier, C. C. et al., "Comparison of antiadhesive treatments using an objective rat model," Am Surg., 65 (3): 274-282, 1999.
Zong, X. et al., "Prevention of Postsurgery-Induced Abdominal Adhesions by Electrospun Bioabsorbable Nanofibrous Poly(lactide-co-glycolide)-Based Membranes," Ann Surg, 240(5):910-915, 2004.

* cited by examiner

POLYPEPTIDE FOR TREATING OR PREVENTING ADHESIONS

CROSS REFERENCE TO RELATED APPLICATIONS

This application claims the benefit of priority of U.S. Application 61/106,834, filed Oct. 20, 2008, and is a continuation-in-part of U.S. application Ser. No. 11/972,459, filed Jan. 10, 2008, which claims priority to U.S. Provisional Application No. 60/880,137 filed Jan. 10, 2007. Each of these applications is incorporated by reference herein in its entirety.

STATEMENT OF GOVERNMENT FUNDING

This invention was made with government support under NIH/NHLBI Grant Number K25 HL074968 awarded by the National Institute of Health. The government has certain rights in the invention.

FIELD OF THE INVENTION

The invention is in the fields of cell and molecular biology, polypeptides, and therapeutic methods of use.

BACKGROUND OF THE INVENTION

1. Adhesions

An adhesion is a band of scar tissue, which binds together two anatomic surfaces normally separated from each other, that develops after surgery, inflammation, or injury. Adhesions may appear as thin sheets of tissue or as thick fibrous bands. Depending on the tissues involved, adhesions may cause various disorders. In the eye, for example, adhesion of the iris to the lens can lead to glaucoma.

Adhesions can occur anywhere. The most common locations are within the abdomen, the pelvis, and the heart.

Abdominal adhesions are a common complication of abdominal or pelvic surgery, and also occur in subjects who never have had surgery. Adhesions also may occur in subjects who develop peritonitis, an infection that has spread to the peritoneum, the membrane that covers the abdominal organs, which commonly occurs after appendicitis or another abdominal infection. In the intestines, adhesions can cause partial or complete bowel obstructions in adults and are believed to contribute to the development of chronic pelvic pain.

Abdominal adhesions typically begin to form within the first few days after surgery, but they may not produce symptoms for months or even years. As scar tissue begins to restrict motion of the small intestines, passing food through the digestive system becomes progressively more difficult, and the bowel may become blocked. In extreme cases, adhesions may form fibrous bands around a segment of an intestine, which constricts blood flow and leads to tissue death.

Pelvic adhesions may involve any organ within the pelvis, such as the uterus, ovaries, fallopian tubes, or bladder, and usually occur after surgery. Pelvic inflammatory disease (PID) results from an infection (usually a sexually transmitted disease) that frequently leads to adhesions within the fallopian tubes. Fallopian adhesions can lead to infertility and an increased incidence of ectopic pregnancy. Endometriosis, an inflammatory condition that also may involve the abdomen and serious abdominal trauma, also may cause adhesions.

Scar tissue also may form within the pericardial sac, the membranes that surround the heart, thus restricting heart function, for example, as a result of a bacterial, viral or fungal infection, serious chest injury, or heart surgery. In acute constrictive pericarditis, for example, the pericardium is covered with a dense mass of calcified fibrosis material. Infections, such as rheumatic fever, may lead to adhesions forming on heart values, leading to decreased heart efficiency.

2. Reduction of Morbidity and Mortality

Methods to prevent adhesions are not known. Abdominal adhesions can be treated, but they can be a recurring problem because surgery is both the cause and the treatment. Most, if not all, agents noted to be effective in reducing adhesion formation have had detrimental effects on bowel anastomotic healing.

Inadequate healing and subsequent leakage of bowel anastomoses are serious postoperative complications in abdominal surgery. Enteric anastomotic complications (EACs) include, but are not limited to, leaks, fistulae (meaning a condition that occurs when two hollow sections, such as areas of the intestines, form an abnormal connection), and intra-abdominal abscesses (meaning an infected pocket of fluid and pus located inside the abdominal cavity).

Intestinal fistulae often are associated with dense adhesions. The fistulae may be enteroenteric, enterocutaneous, enterovesical, enterocolic or enterovaginal. Fistulae can be iatrogenic, such as following operative complication or may be from some other process, including diverticulitis or inflammatory bowel disease.

Stomas (surgically created openings of the bowel or urinary tract to a body surface) and the adhesions around them also can create complexity.

Although adhesions can be quite cumbersome to the surgeon, more importantly their presence can have significant consequences for the patient. Intestinal adhesions have been associated with many conditions for patients including chronic abdominal pain and small bowel obstruction. The presence of intra-abdominal adhesions and their consequences may lead to the need for surgery, perhaps with small bowel resection.

In patients with significant intra-abdominal adhesions, the ureters often become obscured from direct vision and can even become involved in an adhesive mass of bowel, increasing the risk of injury to the ureters. Other potential injuries include injury of the large blood vessels, the bowel and the bladder. Solid organ injuries also potentially complicate operations in patients with extensive intra-abdominal adhesions. After surgery, infectious, or inflammatory processes, adhesions may form, from the bowel to the liver and spleen. The surgeon must use caution to avoid retraction of the bowel as it may be attached to either organ by adhesions. This problem is often seen in patients following cholecystectomy. Multiple, often dense, adhesions are encountered during a right hemi-colectomy. The hepatic flexure or transverse colon can have adhesions to the liver capsule in the area of the gallbladder fossa and even the duodenum can be involved. Retraction of the colon, whether laparoscopic or through laparotomy, can lead to traction on the liver capsule, which can result in a capsular tear and significant bleeding. The duodenum also can be injured during this dissection especially in patients with diverticular disease or colitis. Often, diverticular disease involves the splenic flexure and adhesions from the splenic flexure to the spleen complicate an already potentially difficult dissection. Extra care therefore must be used during the mobilization of the flexure as again retraction of the bowel can result in a capsular tear of the spleen leading to potential haemorrhage or even requiring splenectomy.

The consequences of these adhesions can be so severe that significant morbidity and mortality can result. Adhesions can increase the length and complexity of surgery significantly, and such surgery can be followed postoperatively by enterocutaneous fistula, short-bowel syndrome and markedly prolonged ileus.

Moreover, even after extensive and complete adhesiolysis (meaning surgery to separate or remove adhesions), new adhesion formation may occur and result in additional hospitalizations and operations. Clearly the discomfort, disability and costs are significant. In this era of increased focus on healthcare costs, intestinal adhesions contribute to over $1 billion annually in the United States alone.

Surgeons have been trying to develop strategies and products to prevent the production of adhesions, or at least to reduce their severity and/or quantity. They have tried different agents and techniques but have had little success. In the last decade or so, new technology, like laparoscopy, and new products, such as Seprafilm (Genzyme, Cambridge, Mass.), have played an important role in reducing postoperative intra-abdominal adhesions.

Notwithstanding that these advances, among others, have made a difference in the pathological nature of this process, adhesions remain a very significant challenge to both patients and surgeons (Jobanputra, S, and Wexner, S D *Colorectal Dis.* 2007 October; 9 Suppl 2: 54-9). The presence of intra-abdominal adhesions can create very complex situations that require careful preoperative planning, meticulous intra-operative technique, and detailed postoperative management.

2.1. Causes of Complex Cases

The pathophysiology of adhesions is complex. Since the majority of adhesions are postoperative, surgical technique is the most common cause of intra-abdominal adhesions. Any time a tissue plane is violated, the body's natural reaction is to respond with the formation of scar tissue; in the case of the peritoneal cavity, the result is adhesions. Multiple practices have been associated with worsening this problem ranging from handling the small bowel to poor technique. Other factors that have been found to be responsible include damage to the serosal surface of the intestinal wall, powder from surgical gloves, the type of suture material used, and the extent of devitalized tissue Therefore postoperative adhesions are the focus of most of the new innovations in adhesion prevention.

Inflammation is another cause of adhesions that can make surgery more complex. Patients with inflammatory diseases develop intra-abdominal adhesions in response to the inflammation. These adhesions are often encountered during laparotomy or laparoscopy. This patient population can be extremely difficult to manage not only because of their adhesions but also because their postoperative management may be complicated by external factors, such as steroid and other anti-inflammatory medication use. For example, immune suppression and malnutrition are not uncommon particularly in patients with inflammatory bowel disease.

Diverticular disease, one of the more common infectious processes that lead to adhesion formation, can turn an anterior resection, whether by laparoscopy or conventional laparotomy, into a more complex case. It probably is the most common complex case secondary to adhesions encountered by the general surgeon in the community, second only to adhesive small bowel obstruction. Other common intra-abdominal infectious processes that can lead to adhesion formation include previous episodes of pelvic inflammatory disease, cholecystitis and appendicitis.

External-beam radiation therapy also has been associated with adhesions, although the mechanism of adhesion formation has been less well studied. The effect of external-beam radiation on existing intra-abdominal adhesions is well known; in particular, adhesions following radiotherapy tend to be more vascular, more extensive and more fibrotic compared with nonradiated adhesions.

Weibel, et al. (Weibel, M A and Majano, G. *Am. J. Surg.* 1973; 126: 345-53), who described the relationship of increased age to formation of adhesions, described an increased incidence of spontaneous adhesions in patients over the age of 60. The significance of these adhesions is not well understood but is likely due to inflammatory or infectious processes.

When the decision is made to proceed with surgery in a patient in which a high likelihood of intra-abdominal adhesions exists, careful preoperative planning is required to reduce morbidity and mortality. The presence of intra-abdominal adhesions can make any surgical case a more complex and time consuming one with the potential of significant postoperative morbidity. Therefore pre- and intra-operative preventative measures are considered superior to therapeutic postoperative treatment.

Intra-abdominal adhesive disease, regardless of the aetiology, can be a tremendous burden to the patient and surgeon. Adhesions can convert any procedure into a complex one riddled with potential pitfalls which can have severe adverse sequelae for the patient. It is the duty of the surgeon to use careful judgment and all available techniques to avoid these consequences.

The described invention addresses these problems.

SUMMARY OF THE INVENTION

According to one aspect, the described invention provides a composition to treat or prevent adhesions in a subject in need thereof comprising an adhesion preventing amount of a polypeptide having the sequence YARAAARQARAKALARQLGVAA [SEQ ID NO: 1] and a pharmaceutically acceptable carrier. According to one embodiment, the adhesion is an abdominal adhesion. According to another embodiment, the adhesion is a pelvic adhesion. According to another embodiment, the adhesion is a cardiac adhesion. According to another embodiment, the composition is applied topically. According to another embodiment, the composition is applied topically by means of a biomedical device. According to another embodiment, the composition is applied parenterally. According to another embodiment, the composition is applied parenterally by means of a biomedical device.

According to another aspect, the described invention provides a biomedical device for treating or preventing an adhesion, comprising an adhesion preventing amount of a polypeptide having the sequence YARAAARQARAKALARQLGVAA (SEQ ID NO: 1) disposed on or in the device. According to one embodiment, the adhesion is an abdominal adhesion. According to another embodiment, the adhesion is a pelvic adhesion. According to another embodiment, the adhesion is a cardiac adhesion. According to another embodiment, the polypeptide is disposed in a matrix disposed on the device. According to another embodiment, the matrix is a heparin coating.

According to another aspect, the described invention provides a method for preventing an adhesion in a subject in need thereof, the method comprising the step of (a) administering a therapeutically effective amount of a composition comprising an adhesion preventing amount of a polypeptide of YARAAARQARAKALARQLGVAA [SEQ ID NO: 1] and a pharmaceutically acceptable carrier. According to one embodiment, the adhesion results from surgical intervention. According to another embodiment, the adhesion is an abdominal adhesion. According to another embodiment, the adhesion is a pelvic adhesion. According to another embodiment, the adhesion is a cardiac adhesion. According to another embodiment, the adhesion is a small intestine adhesion. According to another embodiment, the adhesion is a large intestine adhesion.

According to another aspect, the described invention provides a method for treating an existing adhesion scar, the method comprises the steps: (a) surgically excising the adhesion scar after its formation; (b) reconnecting excised surfaces; (c) treating the excision site with the composition of the invention; (d) allowing the excision site to heal in the presence of the composition; whereby the existing adhesion scar is reduced. According to one embodiment, the method further comprises the steps of: (i) monitoring a level of at least one biomarker in a target tissue, wherein the at least one biomarker is selected from the group consisting of: TGFβ1 expression; collagen I expression; CTGF expression; α-smooth muscle actin expression; TNF-α; IL-1; IL-6; IL-8; COX-2; MIP-1α; and MIP-2; and (ii) maintaining the level of the biomarker in the target tissue substantially at normal levels during treatment.

According to another aspect, the described invention provides a composition for treating or preventing an adhesion comprising an isolated nucleic acid that encodes a polypeptide with at least 85% amino acid sequence identity to [SEQ ID NO: 1], wherein the polypeptide prevents adhesions. According to one embodiment, the isolated nucleic acid encodes a polypeptide with at least 95% amino acid sequence identity to [SEQ ID NO: 1]. According to another embodiment, the isolated nucleic acid encodes a polypeptide with at least 100% amino acid sequence identity to [SEQ ID NO: 1], wherein the polypeptide prevents abdominal adhesions.

DETAILED DESCRIPTION OF THE INVENTION

The described invention provides compositions and methods for treating or preventing adhesions in a subject in need thereof, the method comprising the step of (a) administering an adhesion-reducing amount of a composition comprising a polypeptide having the amino acid sequence YARAAAR-QARAKALARQLGVAA [SEQ ID NO: 1] or a functional equivalent thereof and a carrier. The methods are clinically useful for reducing formation of abdominal adhesions initially and for therapeutic treatment of existing scars.

The single letter designation for amino acids is used predominately herein. As is well known by one of skill in the art, such single letter designations are as follows:

A is alanine; C is cysteine; D is aspartic acid; E is glutamic acid; F is phenylalanine; G is glycine; His histidine; I is isoleucine; K is lysine; L is leucine; M is methionine; N is asparagine; P is proline; Q is glutamine; R is arginine; S is serine; T is threonine; V is valine; W is tryptophan; and Y is tyrosine.

The term "anastomosis" as used herein refers to the connection of two tubular structures, such as loops of intestine. A surgical anastomosis occurs when a segment of intestine is resected and the two remaining ends are sewn or stapled together (anastomosed). The procedure is referred to as intestinal anastomosis. Pathological anastomoses that result from trauma or disease and may involve veins, arteries, or intestines usually are referred to as fistulas. In the cases of veins or arteries, traumatic fistulas usually occur between artery and vein. Traumatic intestinal fistulas usually occur between two loops of intestine (entero-enteric fistula) or intestine and skin (enterocutaneous fistula).

The term "disease" or "disorder", as used herein, refers to an impairment of health or a condition of abnormal functioning. The term "syndrome," as used herein, refers to a pattern of symptoms indicative of some disease or condition. The term "injury," as used herein, refers to damage or harm to a structure or function of the body caused by an outside agent or force, which may be physical or chemical. The term "condition", as used herein, refers to a variety of health states and is meant to include disorders or diseases caused by any underlying mechanism or disorder, injury, and the promotion of healthy tissues and organs.

The term an "individual in need thereof" is used to refer to an individual that has suffered or will suffer (for example, via a surgical procedure) a wound that may result in adhesion formation, or has resulted in adhesion formation.

The term "inflammation" as used herein refers to a physiologic response to infection and injury in which cells involved in detoxification and repair are mobilized to the compromised site by inflammatory mediators. The classic signs of inflammation are pain (dolor), heat (calor), redness (rubor), swelling (tumor), and loss of function (functio laesa). Histologically, inflammation involves a complex series of events, including dilatation of arterioles, capillaries, and venules, with increased permeability and blood flow; exudation of fluids, including plasma proteins; and leukocytic migration into the inflammatory focus.

The term "acute inflammation" as used herein, refers to inflammation, usually of sudden onset, characterized by the classical signs, with predominance of the vascular and exudative processes.

The term "chronic inflammation" as used herein refers to inflammation of slow progress and marked chiefly by the formation of new connective tissue; it may be a continuation of an acute form or a prolonged low-grade form, and usually causes permanent tissue damage.

Regardless of the initiating agent, the physiologic changes accompanying acute inflammation encompass four main features: (1) vasodilation, which results in a net increase in blood flow, is one of the earliest physical responses to acute tissue injury; (2) in response to inflammatory stimuli, endothelial cells lining the venules contract, widening the intracellular junctions to produce gaps, leading to increased vascular permeability which permits leakage of plasma proteins and blood cells out of blood vessels; (3) inflammation often is characterized by a strong infiltration of leukocytes at the site of inflammation, particularly neutrophils (polymorphonuclear cells). These cells promote tissue damage by releasing toxic substances at the vascular wall or in uninjured tissue; and (4) fever, produced by pyrogens released from leukocytes in response to specific stimuli.

During the inflammatory process, soluble inflammatory mediators of the inflammatory response work together with cellular components in a systemic fashion in the attempt to contain and eliminate the agents causing physical distress. The term "inflammatory mediators" as used herein refers to the molecular mediators of the inflammatory process. These soluble, diffusible molecules act both locally at the site of tissue damage and infection and at more distant sites. Some inflammatory mediators are activated by the inflammatory process, while others are synthesized and/or released from cellular sources in response to acute inflammation or by other soluble inflammatory mediators. Examples of inflammatory mediators of the inflammatory response include, but are not limited to, plasma proteases, complement, kinins, clotting and fibrinolytic proteins, lipid mediators, prostaglandins, leukotrienes, platelet-activating factor (PAF), peptides and amines, including, but not limited to, histamine, serotonin, and neuropeptides, proinflammatory cytokines, including, but not limited to, interleukin-1, interleukin-4, interleukin-6, interleukin-8, tumor necrosis factor (TNF), interferon-gamma, and interleukin 12.

The term "intestine" is used to refer to the segment of the digestive tract extending from the stomach to the anus and, in humans and other mammals, consists of two segments, the small intestine and the large intestine. In humans, the small intestine is further subdivided into the duodenum, jejunum, and ileum, while the large intestine is subdivided into the cecum and colon.

The term "modulate" as used herein means to regulate, alter, adapt, or adjust to a certain measure or proportion.

The terms "reduce" or "reducing" as used herein refer to limit occurrence of a disorder in individuals at risk of developing the disorder.

The phrase "reducing scar formation" as used herein refers any decrease in scar formation that provides a therapeutic or cosmetic benefit to the patient. Such a therapeutic or cosmetic benefit may be achieved, for example, by decreasing the size and/or depth of a scar relative to scar formation in the absence of treatment with the methods of the invention, or by reducing the size of an existing scar. As used herein, such scars include adhesion formation between organ surfaces, including, but not limited to, those occurring as a result of surgery.

The terms "subject" or "individual" are used interchangeably to refer to a member of an animal species of mammalian origin, including humans.

The terms "treat" or "treating" as used herein refer to accomplishing one or more of the following: (a) reducing the severity of the disorder; (b) limiting development of symptoms characteristic of the disorder(s) being treated; (c) limiting worsening of symptoms characteristic of the disorder(s) being treated; (d) limiting recurrence of the disorder(s) in patients that have previously had the disorder(s); and (e) limiting recurrence of symptoms in patients that were previously symptomatic for the disorder(s).

The term "wound" as used herein refers broadly to injuries to the subcutaneous tissue. Such wounds include, but are not limited to fistulas; ulcers; lesions caused by infections; laparotomy wounds; surgical wounds; incisional wounds; and heart tissue fibrosis.

When referring to animals, that typically have one end with a head and mouth, with the opposite end often having the anus and tail, the head end is referred to as the cranial end, while the tail end is referred to as the caudal end. Within the head itself, rostral refers to the direction toward the end of the nose, and caudal is used to refer to the tail direction. The surface or side of an animal's body that is normally oriented upwards, away from the pull of gravity, is the dorsal side; the opposite side, typically the one closest to the ground when walking on all legs, swimming or flying, is the ventral side. On the limbs or other appendages, a point closer to the main body is "proximal"; a point farther away is "distal". Three basic reference planes are used in zoological anatomy. A "sagittal" plane divides the body into left and right portions. The "midsagittal" plane is in the midline, i.e. it would pass through midline structures such as the spine, and all other sagittal planes are parallel to it. A "coronal" plane divides the body into dorsal and ventral portions. A "transverse" plane divides the body into cranial and caudal portions.

When referring to humans, the body and its parts are always described using the assumption that the body is standing upright. Portions of the body which are closer to the head end are "superior" (corresponding to cranial in animals), while those farther away are "inferior" (corresponding to caudal in animals). Objects near the front of the body are referred to as "anterior" (corresponding to ventral in animals); those near the rear of the body are referred to as "posterior" (corresponding to dorsal in animals). A transverse, axial, or horizontal plane is an X-Y plane, parallel to the ground, which separates the superior/head from the inferior/feet. A coronal or frontal plane is an Y-Z plane, perpendicular to the ground, which separates the anterior from the posterior. A sagittal plane is an X-Z plane, perpendicular to the ground and to the coronal plane, which separates left from right. The midsagittal plane is the specific sagittal plane that is exactly in the middle of the body.

Structures near the midline are called medial and those near the sides of animals are called lateral. Therefore, medial structures are closer to the midsagittal plane, lateral structures are further from the midsagittal plane. Structures in the midline of the body are median. For example, the tip of a human subject's nose is in the median line.

Ipsilateral means on the same side, contralateral means on the other side and bilateral means on both sides. Structures that are close to the center of the body are proximal or central, while ones more distant are distal or peripheral. For example, the hands are at the distal end of the arms, while the shoulders are at the proximal ends.

In one aspect, the described invention provides a composition for treating or preventing the formation of adhesions in a subject in need thereof comprising a therapeutically effective amount of a polypeptide having the amino acid sequence YARAAARQARAKALARQLGVAA [SEQ ID NO: 1] or a functional equivalent thereof and a pharmaceutically acceptable carrier. Such pharmaceutical compositions are especially useful for carrying out the methods of the invention described below.

The term "active" refers to the ingredient, component or constituent of the compositions of the described invention responsible for the intended therapeutic effect.

A "pharmaceutical composition" is one that is employed to prevent, reduce in intensity, cure, or otherwise treat a target condition, syndrome, disorder or disease that has undergone federal regulatory review.

The term "pharmaceutically acceptable carrier" as used herein refers to any substantially non-toxic carrier conventionally useable for administration of pharmaceuticals in which the isolated polypeptide of the described invention will remain stable and bioavailable.

The term "peptide" is used herein to refer to two or more amino acids joined by a peptide bond.

The term "polypeptide" is used in its broadest sense to refer to a sequence of subunit amino acids, amino acid analogs, or peptidomimetics. The subunits are linked by peptide bonds, except where noted. The polypeptide described herein may be chemically synthesized or recombinantly expressed.

The term "protein" is used herein to refer to a large complex molecule or polypeptide composed of amino acids. The sequence of the amino acids in the protein is determined by the sequence of the bases in the nucleic acid sequence that encodes it.

The terms "peptide", "polypeptide" and "protein" also apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein that protein is specifically reactive to antibodies elicited to the same protein but consisting entirely of naturally occurring amino acids. The terms "polypeptide", "peptide" and "protein" also are inclusive of modifications including, but not limited to, glycosylation, lipid attachment, sulfation, gamma-carboxylation of glutamic acid residues, hydroxylation and ADP-ribosylation. It will be appreciated, as is well known and as noted above, that polypeptides may not be entirely linear. For instance, polypeptides may be branched as a result of ubiquitination, and they may be circular, with or without branching, generally as a result of posttranslational events, including natural processing event and events brought about by human manipulation which do not occur naturally. Circular, branched and branched circular polypeptides may be synthesized by nontranslation natural process and by entirely synthetic methods, as well.

The terms "residue" or "amino acid residue" or "amino acid" are used interchangeably to refer to an amino acid that is incorporated into a protein, a polypeptide, or a peptide, including, but not limited to, a naturally occurring amino acid and known analogs of natural amino acids that can function in a similar manner as naturally occurring amino acids.

The terms "variants", "mutants", and "derivatives" are used herein to refer to nucleotide sequences with substantial identity to a reference nucleotide sequence. The differences in the sequences may by the result of changes, either naturally or by design, in sequence or structure. Natural changes may arise during the course of normal replication or duplication in nature of the particular nucleic acid sequence. Designed changes may be specifically designed and introduced into the sequence for specific purposes. Such specific changes may be made in vitro using a variety of mutagenesis techniques. Such sequence variants generated specifically may be referred to as "mutants" or "derivatives" of the original sequence.

A skilled artisan likewise can produce polypeptide variants having single or multiple amino acid substitutions, deletions, additions or replacements. These variants may include inter alia: (a) variants in which one or more amino acid residues are substituted with conservative or non-conservative amino acids; (b) variants in which one or more amino acids are added; (c) variants in which at least one amino acid includes a substituent group; (d) variants in which amino acid residues from one species are substituted for the corresponding residue in another species, either at conserved or non-conserved positions; and (d) variants in which a target protein is fused with another peptide or polypeptide such as a fusion partner, a protein tag or other chemical moiety, that may confer useful properties to the target protein, such as, for example, an epitope for an antibody. The techniques for obtaining such variants, including genetic (suppressions, deletions, mutations, etc.), chemical, and enzymatic techniques are known to the skilled artisan. As used herein, the term "mutation" refers to a change of the DNA sequence within a gene or chromosome of an organism resulting in the creation of a new character or trait not found in the parental type, or the process by which such a change occurs in a chromosome, either through an alteration in the nucleotide sequence of the DNA coding for a gene or through a change in the physical arrangement of a chromosome. Three mechanisms of mutation include substitution (exchange of one base pair for another), addition (the insertion of one or more bases into a sequence), and deletion (loss of one or more base pairs).

The term "substitution" is used herein to refer to that in which a base or bases are exchanged for another base or bases in the DNA. Substitutions may be synonymous substitutions or nonsynonymous substitutions. As used herein, "synonymous substitutions" refer to substitutions of one base for another in an exon of a gene coding for a protein, such that the amino acid sequence produced is not modified. The term "nonsynonymous substitutions" as used herein refer to substitutions of one base for another in an exon of a gene coding for a protein, such that the amino acid sequence produced is modified.

The terms "deletion" and "deletion mutation" are used interchangeably herein to refer to that in which a base or bases are lost from the DNA.

The term "addition" as used herein refers to the insertion of one or more bases, or of one or more amino acids, into a sequence.

The following represent groups of amino acids that are conservative substitutions for one another:
1) Alanine (A), Serine (S), Threonine (T);
2) Aspartic Acid (D), Glutamic Acid (E);
3) Asparagine (N), Glutamic Acid (O);
4) Arginine (R), Lysine (K); 5) Isoleucine (I), Leucine (L), Methionine (M), Valine (V); and
6) Phenylalanine (F), Tyrosine (Y), Tryptophan (W).

The term "similar" is used interchangeably with the terms analogous, comparable, or resembling, meaning having traits or characteristics in common.

In some embodiments, the polypeptide of the described invention is chemically synthesized. Such a synthetic polypeptide, prepared using the well known techniques of solid phase, liquid phase, or peptide condensation techniques, or any combination thereof, may include natural and unnatural amino acids. Amino acids used for peptide synthesis may be standard Boc (N-α-amino protected N-α-t-butyloxycarbonyl) amino acid resin with the standard deprotecting, neutralization, coupling and wash protocols of the original solid phase procedure of Merrifield (1963, J. Am. Chem. Soc. 85:2149-2154), or the base-labile N-α-amino protected 9-fluorenylmethoxycarbonyl (Fmoc) amino acids first described by Carpino and Han (1972, J. Org. Chem. 37:3403-3409). Both Fmoc and Boc N-α-amino protected amino acids can be obtained from Sigma, Cambridge Research Biochemical, or other chemical companies familiar to those skilled in the art. In addition, the polypeptide may be synthesized with other N-α-protecting groups that are familiar to those skilled in this art.

Solid phase peptide synthesis may be accomplished by techniques familiar to those in the art and provided, for example, in Stewart and Young, 1984, Solid Phase Synthesis, Second Edition, Pierce Chemical Co., Rockford, Ill.; Fields and Noble, 1990, Int. J. Pept. Protein Res. 35:161-214, or using automated synthesizers.

The term "functional equivalent" as used herein refers to substances, molecules, proteins, peptides or polypeptides having similar or identical effects or use. A functionally equivalent polypeptide of the polypeptide [SEQ ID NO: 1] may have similar or identical activity, similar or identical inhibition activity, kinetic parameters, salt inhibition, cofactor-dependent activity, and a functional unit size very similar to the expressed polypeptide [SEQ ID NO: 1].

In some embodiments, the polypeptide of the invention may comprise D-amino acids (which are resistant to L-amino acid-specific proteases in vivo), a combination of D- and L-amino acids, and various "designer" amino acids (e.g., (β-methyl amino acids, C-α-methyl amino acids, and N-α-methyl amino acids, etc.) to convey special properties. Synthetic amino acids include ornithine for lysine, and norleucine for leucine or isoleucine.

In addition, the polypeptide of the described invention may have peptidomimetic bonds, such as ester bonds, to prepare peptides with novel properties. For example, a peptide may be generated that incorporates a reduced Peptide bond, i.e., $R_1$—$CH_2$—NH—$R_2$, where $R_1$ and $R_2$ are amino acid residues or sequences. A reduced peptide bond may be introduced as a dipeptide subunit. Such a polypeptide would be resistant to protease activity, and would possess an extended half-live in vivo.

In another embodiment, the described invention provides an isolated nucleic acid that encodes a polypeptide with at least 85% amino acid sequence identity to [SEQ ID NO: 1]. In some such embodiments, the described invention provides an isolated nucleic acid that encodes a polypeptide with at least 95% amino acid sequence identity to [SEQ ID NO. 1]. In some such embodiments, the described invention provides an isolated nucleic acid that encodes a polypeptide with at least 100% amino acid sequence identity to [SEQ ID NO. 1]. In another embodiment, the described invention provides an isolated nucleic acid that encodes a polypeptide with at least 85% amino acid sequence identity to [SEQ ID NO: 1], wherein the polypeptide prevents abdominal adhesions. In another embodiment, the described invention provides an isolated nucleic acid that encodes a polypeptide with at least 95% amino acid sequence identity to [SEQ ID NO: 1], wherein the polypeptide prevents abdominal adhesions. In another embodiment, the described invention provides an isolated nucleic acid that encodes a polypeptide with at least 100% amino acid sequence identity to [SEQ ID NO: 1], wherein the polypeptide prevents abdominal adhesions.

The term "isolated" is used herein to refer to material, such as, but not limited to, a nucleic acid, peptide, polypeptide, or protein, which is: (1) substantially or essentially free from components that normally accompany or interact with it as found in its naturally occurring environment. The terms "substantially free" or "essentially free" are used herein to refer to considerably or significantly free of or more than about 95% free of, or more than about 99% free of. The isolated material optionally comprises material not found with the material in its natural environment; or (2) if the material is in its natural environment, the material has been synthetically (non-naturally) altered by deliberate human intervention to a composition and/or placed at a location in the cell (e.g., genome or subcellular organelle) not native to a material found in that environment. The alteration to yield the synthetic material may be performed on the material within, or removed, from its natural state. For example, a naturally occurring nucleic acid becomes an isolated nucleic acid if it is altered, or if it is transcribed from DNA that has been altered, by means of human intervention performed within the cell from which it originates. See, for example, Compounds and Methods for Site Directed Mutagenesis in Eukaryotic Cells, Kmiec, U.S. Pat. No. 5,565,350; In Vivo Homologous Sequence Targeting in Eukaryotic Cells; Zarling et al., PCT/US93/03868. Likewise, a naturally occurring nucleic acid (for example, a promoter) becomes isolated if it is introduced by non-naturally occurring means to a locus of the genome not native to that nucleic acid. Nucleic acids that are "isolated" as defined herein also are referred to as "heterologous" nucleic acids.

The term "nucleic acid" is used herein to refer to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

The term "nucleotide" is used herein to refer to a chemical compound that consists of a heterocyclic base, a sugar, and one or more phosphate groups. In the most common nucleotides, the base is a derivative of purine or pyrimidine, and the sugar is the pentose deoxyribose or ribose. Nucleotides are the monomers of nucleic acids, with three or more bonding together in order to form a nucleic acid. Nucleotides are the structural units of RNA, DNA, and several cofactors, including, but not limited to, CoA, FAD, DMN, NAD, and NADP. Purines include adenine (A), and guanine (G); pyrimidines include cytosine (C), thymine (T), and uracil (U).

The following terms are used herein to describe the sequence relationships between two or more nucleic acids or polynucleotides: (a) "reference sequence", (b) "comparison window", (c) "sequence identity", (d) "percentage of sequence identity", and (e) "substantial identity".

The term "reference sequence" refers to a sequence used as a basis for sequence comparison. A reference sequence may be a subset or the entirety of a specified sequence; for example, as a segment of a full-length cDNA or gene sequence, or the complete cDNA or gene sequence.

The term "comparison window" refers to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be at least 30 contiguous nucleotides in length, at least 40 contiguous nucleotides in length, at least 50 contiguous nucleotides in length, at least 100 contiguous nucleotides in length, or longer. Those of skill in the art understand that to avoid a high similarity to a reference sequence due to inclusion of gaps in the polynucleotide sequence, a gap penalty typically is introduced and is subtracted from the number of matches.

Methods of alignment of sequences for comparison are well-known in the art. Optimal alignment of sequences for comparison may be conducted by the local homology algorithm of Smith and Waterman, Adv. Appl. Math. 2:482 (1981); by the homology alignment algorithm of Needleman and Wunsch, J. Mol. Biol. 48:443 (1970); by the search for similarity method of Pearson and Lipman, Proc. Natl. Acad. Sci. 85:2444 (1988); by computerized implementations of these algorithms, including, but not limited to: CLUSTAL in the PC/Gene program by Intelligenetics, Mountain View, Calif.; GAP, BESTFIT, BLAST, FASTA, and TFASTA in the Wisconsin Genetics Software Package, Genetics Computer Group (GCG), 575 Science Dr., Madison, Wis., USA; the CLUSTAL program is well described by Higgins and Sharp, Gene 73:237-244 (1988); Higgins and Sharp, CABIOS 5:151-153 (1989); Corpet, et al., Nucleic Acids Research 16:10881-90 (1988); Huang, et al., Computer Applications in the Biosciences 8:155-65 (1992), and Pearson, et al., Methods in Molecular Biology 24:307-331 (1994). The BLAST family of programs, which can be used for database similarity searches, includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, Current Protocols in Molecular Biology, Chapter 19, Ausubel, et al., Eds., Greene Publishing and Wiley-Interscience, New York (1995).

Unless otherwise stated, sequence identity/similarity values provided herein refer to the value obtained using the BLAST 2.0 suite of programs using default parameters. Altschul et al., Nucleic Acids Res. 25:3389-3402 (1997). Software for performing BLAST analyses is publicly available, e.g., through the National Center for Biotechnology-Information on the world wide web (www) at the URL "ncbi.nlm.nih.gov." This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits then are extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, a cutoff of 100, M=5, N=−4, and a comparison of both strands. For amino acid sequences, the BLASTP program uses as defaults a word length (W) of 3, an expectation (E) of 10, and the BLOSUM62 scoring matrix (see Henikoff & Henikoff (1989) Proc. Natl. Acad. Sci. USA 89:10915).

In addition to calculating percent sequence identity, the BLAST algorithm also performs a statistical analysis of the similarity between two sequences (see, e.g., Karlin & Altschul, Proc. Natl. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. BLAST searches assume that proteins may be modeled as random sequences. However, many real proteins comprise regions of nonrandom sequences which may be homopolymeric tracts, short-period repeats, or regions enriched in one or more amino acids. Such low-complexity regions may be aligned between unrelated proteins even though other regions of the protein are entirely dissimilar. A number of low-complexity filter programs may be employed to reduce such low-complexity alignments. For example, the SEG (Wooten and Federhen, Comput. Chem., 17:149-163 (1993)) and XNU (Claverie and States, Comput. Chem., 17:191-201 (1993)) low-complexity filters may be employed alone or in combination.

The term "sequence identity" or "identity" in the context of two nucleic acid or polypeptide sequences is used herein to refer to the residues in the two sequences that are the same when aligned for maximum correspondence over a specified comparison window. When percentage of sequence identity is used in reference to proteins it is recognized that residue positions that are not identical often differ by conservative amino acid substitutions, i.e., where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, Computer Applic. Biol. Sci., 4:11-17 (1988) e.g., as implemented in the program PC/GENE (Intelligenetics, Mountain View, Calif., USA).

The term "percentage of sequence identity" is used herein mean the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The term "substantial identity" of polynucleotide sequences means that a polynucleotide comprises a sequence that has at least 70% sequence identity, at least 80% sequence identity, at least 90% sequence identity and at least 95% sequence identity, compared to a reference sequence using one of the alignment programs described using standard parameters. One of skill will recognize that these values may be adjusted appropriately to determine corresponding identity of proteins encoded by two nucleotide sequences by taking into account codon degeneracy, amino acid similarity, reading frame positioning and the like. Substantial identity of amino acid sequences for these purposes normally means sequence identity of at least 60%, or at least 70%, at least 80%, at least 90%, or at least 95%. Another indication that nucleotide sequences are substantially identical is if two molecules hybridize to each other under stringent conditions. However, nucleic acids that do not hybridize to each other under stringent conditions are still substantially identical if the polypeptides that they encode are substantially identical. This may occur, e.g., when a copy of a nucleic acid is created using the maximum codon degeneracy permitted by the genetic code. One indication that two nucleic acid sequences are substantially identical is that the polypeptide that the first nucleic acid encodes is immunologically cross reactive with the polypeptide encoded by the second nucleic acid.

The terms "substantial identity" in the context of a peptide indicates that a peptide comprises a sequence with at least 70% sequence identity to a reference sequence, at least 80%, at least 85%, at least 90% or 95% sequence identity to the reference sequence over a specified comparison window. Optionally, optimal alignment is conducted using the homology alignment algorithm of Needleman and Wunsch, J. Mol. Biol. 48:443 (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides which are "substantially similar" share sequences as noted above except that residue positions that are not identical may differ by conservative amino acid changes.

In another aspect, the described invention provides methods for treating or preventing adhesions in a subject in need thereof, the method comprising the step of (a) administering a therapeutically effective amount of a composition comprising a polypeptide of SEQ ID NO: 1 or a functional equivalent thereof and a carrier.

For administration, the polypeptide of the described invention ordinarily is combined with one or more carriers appropriate for the indicated route of administration. The terms "carrier" and "pharmaceutical carrier" as used herein refer to a pharmaceutically acceptable inert agent or vehicle for delivering one or more active agents to a subject, and often is referred to as "excipient." The term "vehicle" refers to a substance that facilitates the use of a drug or other material that is mixed with it.

The (pharmaceutical) carrier must be of sufficiently high purity and of sufficiently low toxicity to render it suitable for administration to the subject being treated. The (pharmaceutical) carrier further should maintain the stability and bioavailability of an active agent, e.g., a polypeptide of the described invention. The (pharmaceutical) carrier can be liquid or solid and is selected, with the planned manner of administration in mind, to provide for the desired bulk, consistency, etc., when combined with an active agent and other components of a given composition. The (pharmaceutical) carrier may be, without limitation, a binding agent (e.g., pregelatinized maize starch, polyvinylpyrrolidone or hydroxypropyl methylcellulose, etc.), a filler (e.g., lactose and other sugars, microcrystalline cellulose, pectin, gelatin, calcium sulfate, ethyl cellulose, polyacrylates, calcium hydrogen phosphate, etc.), a lubricant (e.g., magnesium stearate, talc, silica, colloidal silicon dioxide, stearic acid, metallic stearates, hydrogenated vegetable oils, corn starch, polyethylene glycols, sodium benzoate, sodium acetate, etc.), a disintegrant (e.g., starch, sodium starch glycolate, etc.), or a wetting agent (e.g., sodium lauryl sulphate, etc.). Other suitable (pharmaceutical) carriers for the compositions of the described invention include, but are not limited to, water, salt solutions, alcohols, polyethylene glycols, gelatins, amyloses, magnesium stearates, talcs, silicic acids, viscous paraffins, hydroxymethylcelluloses, polyvinylpyrrolidones and the like. Compositions of the described invention that are for parenteral administration of the polypeptide may include (pharmaceutical) carriers such as sterile aqueous solutions, non-aqueous solutions in common solvents such as alcohols, or solutions of the polypeptide in a liquid oil base.

In some embodiments, the carrier of the composition of the described invention includes a release agent such as sustained release or delayed release carrier. In such embodiments, the carrier can be any material capable of sustained or delayed release of the signal transduction modulator compound to provide a more efficient administration, e.g., resulting in less frequent and/or decreased dosage of the compound, improve ease of handling, and extend or delay effects on diseases, disorders, conditions, syndromes, and the like, being treated, prevented or promoted. Non-limiting examples of such carriers include liposomes, microsponges, microspheres, or microcapsules of natural and synthetic polymers and the like. Liposomes may be formed from a variety of phospholipids such as cholesterol, stearylamines or phosphatidylcholines.

The polypeptide may be linked to other compounds to promote an increased half-life in vivo, such as polyethylene glycol. Such linkage can be covalent or non-covalent as is understood by those of skill in the art.

The polypeptide may be prepared in a solid form (including granules, powders or suppositories) or in a liquid form (e.g., solutions, suspensions, or emulsions). The polypeptide of the invention may be applied in a variety of solutions. To be suitable, a formulations is sterile, dissolves sufficient amounts of the polypeptides, and is not harmful for the proposed application.

For example, the compositions of the described invention may be formulated as aqueous suspensions wherein the active ingredient(s) is (are) in admixture with excipients suitable for the manufacture of aqueous suspensions. Such excipients are suspending agents, for example, sodium carboxymethylcellulose, methylcellulose, hydroxy-propylmethylcellulose, sodium alginate, polyvinylpyrrolidone, gum tragacanth, and gum acacia; dispersing or wetting agents may be a naturally-occurring phosphatide such as lecithin, or condensation products of an alkylene oxide with fatty acids, for example, polyoxyethylene stearate, or condensation products of ethylene oxide with long chain aliphatic alcohols, for example, heptadecaethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate.

Compositions of the described invention also may be formulated as oily suspensions by suspending the active ingredient in a vegetable oil, for example arachis oil, olive oil, sesame oil or coconut oil, or in a mineral oil, such as liquid paraffin. The oily suspensions may contain a thickening agent, for example, beeswax, hard paraffin or cetyl alcohol.

Compositions of the described invention also may be formulated in the form of dispersible powders and granules suitable for preparation of an aqueous suspension by the addition of water. The active ingredient in such powders and granules is provided in admixture with a dispersing or wetting agent, suspending agent, and one or more preservatives. Suitable dispersing or wetting agents and suspending agents are exemplified by those already mentioned above. Additional excipients also may be present.

The compositions of the invention also may be in the form of an emulsion. An emulsion is a two-phase system prepared by combining two immiscible liquid carriers, one of which is disbursed uniformly throughout the other and consists of globules that have diameters equal to or greater than those of the largest colloidal particles. The globule size is critical and must be such that the system achieves maximum stability. Usually, separation of the two phases will not occur unless a third substance, an emulsifying agent, is incorporated. Thus, a basic emulsion contains at least three components, the two immiscible liquid carriers and the emulsifying agent, as well as the active ingredient. Most emulsions incorporate an aqueous phase into a non-aqueous phase (or vice versa). However, it is possible to prepare emulsions that are basically non-aqueous, for example, anionic and cationic surfactants of the non-aqueous immiscible system glycerin and olive oil. Thus, the compositions of the invention may be in the form of an oil-in-water emulsion. The oily phase may be a vegetable oil, for example, olive oil or arachis oil, or a mineral oil, for example a liquid paraffin, or a mixture thereof. Suitable emulsifying agents may be naturally-occurring gums, for example, gum acacia or gum tragacanth, naturally-occurring phosphatides, for example soy bean, lecithin, and esters or partial esters derived from fatty acids and hexitol anhydrides, for example sorbitan monooleate, and condensation products of the partial esters with ethylene oxide, for example, polyoxyethylene sorbitan monooleate.

In another aspect, the described invention provides a biomedical device comprising a polypeptide of SEQ ID NO: 1 or a functional equivalent thereof disposed on or in the biomedical device. As used herein, a "biomedical device" refers to a device to be implanted into a subject, for example, a human being, in order to bring about a desired result. Particularly preferred biomedical devices according to this aspect of the invention include, but are not limited to, stents, grafts, shunts, stent grafts, fistulas, angioplasty devices, balloon catheters, venous catheters, implantable drug delivery devices, adhesion barriers (including but not limited to carboxymethylcellulose, hyaluronic acid, and PTFE sheets) to separate tissue, wound dressings such as films (e.g., polyurethane films), hydrocolloids (hydrophilic colloidal particles bound to polyurethane foam), hydrogels (cross-linked polymers containing about at least 60% water), other viscous liquids and hydrogel-like species (including but not limited to, those disclosed in US 20030190364), foams (hydrophilic or hydrophobic), calcium alginates (nonwoven composites of fibers from calcium alginate), cellophane, pluronics (ie: poly(ethylene glycol)-block-poly(propylene glycol), and biological polymers.

The term "grafts" as used herein refers to both natural and prosthetic grafts and implants.

The term "disposed on or in" as used herein means that the one or more polypeptides can be either directly or indirectly in contact with an outer surface, an inner surface, or embedded within the biomedical device. "Direct" contact refers to disposition of the polypeptides directly on or in the device, including but not limited to soaking a biomedical device in a solution containing the one or more polypeptides, spin coating or spraying a solution containing the one or more polypeptides onto the device, implanting any device that would deliver the polypeptide, and administering the polypeptide through a catheter directly on to the surface or into any organ.

"Indirect" contact means that the one or more polypeptides do not directly contact the biomedical device. For example, the one or more polypeptides may be disposed in a matrix, such as a gel matrix (such as a heparin coating) or a viscous fluid, which is disposed on the biomedical device. Such matrices can be prepared to, for example, modify the binding and release properties of the one or more polypeptides as required. In one non-limiting example, a heparin coating is disposed on the biomedical device (such as a poly(tetrafluoroethylene) (PTFE) vascular device or sheet) and the one or more polypeptides are disposed on or in a heparin coating; in this example, the one or more polypeptides can be delivered to a subject in need thereof in a controlled manner. In one non-limiting example, the release of the one or more polypeptides from interstitial surfaces of poly(tetrafluoroethylene) (PTFE) vascular devices or sheets can be controlled by first adsorbing or bonding heparin to the surface and/or interstices of the PTFE device followed by adsorption of polypeptide. Alternating layers of heparin and the polypeptide can also be used to increase the polypeptide dose and/or time of release. Under physiological conditions within the body, the kinetics of the association and dissociation of polypeptides disclosed herein to and from heparin will lead to a delayed release profile as compared to release of the polypeptide from a bare PTFE device. In addition, the release profile can be further altered through changes in local temperature, pH or ionic strength. Such controlled release is of great value for use in the various therapeutic treatments for which the biomedical devices can be used, as discussed below.

Heparin coatings on various medical devices are known in the art. Applications in humans include central venous catheters, coronary stents, ventricular assist devices, extracorporeal blood circuits, blood sampling devices, and vascular grafts. Such coatings can be in a gel or non-gel form. As used herein "heparin coating" includes heparin adsorbed to the surface, heparin bonded to the surface, and heparin imbedded in the PTFE polymer surface. An example of a method for bonding the heparin would be to use ammonia plasma to treat, for example, a PTFE surface and reacting the resultant amines with oxidized heparin. Layer-by-layer buildup of the heparin and one or more polypeptides could then be used to increase polypeptide on the surface and expand the delivery time. Gel forms of the heparin coating can include, but are not limited to, any hydrogel containing heparin either covalently or physically bound to the gel. The heparin coating is disposed on the biomedical device, which includes direct contact with an outer surface or an inner surface of the biomedical device, or embedded within the biomedical device. "Direct" contact refers to disposition directly on or in the device, including but not limited to soaking a biomedical device in a heparin coating solution (wherein the polypeptides may be added as part of the heparin coating solution, or may be subsequently disposed on or in the heparin coating after it is contacted with the device), spin coating or spraying a heparin coating solution onto the device (wherein the polypeptides may be added as part of the heparin coating solution, or may be subsequently disposed on or in the heparin coating after it is contacted with the device), and administering the heparin coating solution containing the polypeptides through a catheter directly on to the surface or into any organ. The physical characteristics and specific composition of the heparin layer can be any that provides the desired release profile of the one or more polypeptides. See, for example, Seal and Panitch, Biomacromolecules 2003(4):1572-1582 (2003); US20030190364, incorporated by reference herein in its entirety; and Carmeda BioActive Surface (CBAS™) the product of Carmeda AB in Stockholm, Sweden. "Indirect" contact means that the heparin coating is not directly in contact with the device such as, for example, when an intervening coating is placed between the device surface and the heparin coating. In one non-limiting example, the one or more polypeptides could be initially adsorbed (directly or indirectly), and then adsorbing a heparin coating; this can optionally be followed by subsequent polypeptide layers, heparin layers, or combinations thereof, as desired. As will be understood by those of skill in the art, any sulfated polysaccharide or negatively charged polymer can be used in like manner to heparin as described above, to provide desired release characteristics.

Without being bound by theory, it is believed that the polypeptide of SEQ ID NO: 1 provides its therapeutic effect at least in part as a result of inhibiting HSP27 phosphorylation by HSP27 kinase (MAPKAP kinase 2). Alternative mechanisms, including, but not limited to, inhibition of HSP27 phosphorylation by MAPKAP kinase 3, and MAPKAP kinase 5 also may contribute to its therapeutic effect. Since MAPKAP2 is downstream of p38 MAP kinase, any therapeutic uses for which p38 MAPK inhibitors are useful are within the scope of the described invention as well.

The term "administering" as used herein includes in vivo administration, as well as administration directly to tissue ex vivo. The compositions of the described invention may be administered systemically either orally, buccally, parenterally, topically, by inhalation or insufflation (i.e., through the mouth or through the nose), or rectally in dosage unit formulations containing conventional nontoxic pharmaceutically acceptable carriers, adjuvants, and vehicles as desired.

The term "parenteral" as used herein refers to introduction into the body by way of an injection (i.e., administration by injection), including, for example, subcutaneously (i.e., an injection beneath the skin), intramuscularly (i.e., an injection into a muscle); intravenously (i.e., an injection into a vein), intrathecally (i.e., an injection into the space around the spinal cord), intrasternal injection, or infusion techniques. A parenterally administered composition of the described invention is delivered using a needle, e.g., a surgical needle. The term "surgical needle" as used herein, refers to any needle adapted for delivery of fluid (i.e., capable of flow) compositions of the described invention into a selected anatomical structure. Injectable preparations, such as sterile injectable aqueous or oleaginous suspensions, may be formulated according to the known art using suitable dispersing or wetting agents and suspending agents.

The sterile injectable preparation also may be a sterile injectable solution or suspension in a nontoxic parenterally acceptable diluent or solvent, for example, as a solution in 1,3-butanediol. A solution generally is considered as a homogeneous mixture of two or more substances; it is frequently, though not necessarily, a liquid. In a solution, the molecules of the solute (or dissolved substance) are uniformly distributed among those of the solvent. A suspension is a dispersion (mixture) in which a finely-divided species is combined with another species, with the former being so finely divided and mixed that it doesn't rapidly settle out. In everyday life, the most common suspensions are those of solids in liquid water. Among the acceptable vehicles and solvents that may be employed are water, Ringer's solution, and isotonic sodium chloride solution. In addition, sterile, fixed oils are conventionally employed as a solvent or suspending medium. For parenteral application, particularly suitable vehicles consist of solutions, preferably oily or aqueous solutions, as well as suspensions, emulsions, or implants. Aqueous suspensions may contain substances which increase the viscosity of the suspension and include, for example, sodium carboxymethyl cellulose, sorbitol and/or dextran. Optionally, the suspension may also contain stabilizers.

The term "topical" as used herein refers to administration of an inventive composition at, or immediately beneath, the point of application. The phrase "topically applying" describes application onto one or more surfaces(s) including epithelial surfaces. Although topical administration, in contrast to transdermal administration, generally provides a local rather than a systemic effect, as used herein, unless otherwise stated or implied, the terms topical administration and transdermal administration are used interchangeably.

Topical administration also may involve the use of transdermal administration such as transdermal patches or iontophoresis devices which are prepared according to techniques and procedures well known in the art. The terms "transdermal delivery system", transdermal patch" or "patch" refer to an adhesive system placed on the skin to deliver a time released dose of a drug(s) by passage from the dosage form through the skin to be available for distribution via the systemic circulation. Transdermal patches are, a well-accepted technology used to deliver a wide variety of pharmaceuticals, including, but not limited to, scopolamine for motion sickness, nitroglycerin for treatment of angina pectoris, clonidine for hypertension, estradiol for post-menopausal indications, and nicotine for smoking cessation. Patches suitable for use in the described invention include, but are not limited to, (1) the matrix patch; (2) the reservoir patch; (3) the multi-laminate drug-in-adhesive patch; and (4) the monolithic drug-in-adhesive patch; TRANSDERMAL AND TOPICAL DRUG DELIVERY SYSTEMS, pp. 249-297 (Tapash K. Ghosh et al. eds., 1997), hereby incorporated herein by reference. These patches are well known in the art and generally available commercially.

The compositions of the described invention may be in the form of a dispersible dry powder for delivery by inhalation or insufflation (either through the mouth or through the nose). Dry powder compositions may be prepared by processes known in the art, such as lyophilization and jet milling, as disclosed in International Patent Publication No. WO 91/16038 and as disclosed in U.S. Pat. No. 6,921,527, the disclosures of which are incorporated by reference. The composition of the described invention is placed within a suitable dosage receptacle in an amount sufficient to provide a subject with a unit dosage treatment. The dosage receptacle is one that fits within a suitable inhalation device to allow for the aerosolization of the dry powder composition by dispersion into a gas stream to form an aerosol and then capturing the aerosol so produced in a chamber having a mouthpiece attached for subsequent inhalation by a subject in need of treatment. Such a dosage receptacle includes any container enclosing the composition known in the art such as gelatin or plastic capsules with a removable portion that allows a stream of gas (e.g., air) to be directed into the container to disperse the dry powder composition. Such containers are exemplified by those shown in U.S. Pat. No. 4,227,522; U.S. Pat. No. 4,192,309; and U.S. Pat. No. 4,105,027. Suitable containers also include those used in conjunction with Glaxo's Ventolin® Rotohaler brand powder inhaler or Fison's Spinhaler® brand powder inhaler. Another suitable unit-dose container which provides a superior moisture barrier is formed from an aluminum foil plastic laminate. The pharmaceutical-based powder is filled by weight or by volume into the depression in the formable foil and hermetically sealed with a covering foil-plastic laminate. Such a container for use with a powder inhalation device is described in U.S. Pat. No. 4,778,054 and is used with Glaxo's Diskhaler® (U.S. Pat. Nos. 4,627,432; 4,811,731; and 5,035,237). All of these references are incorporated herein by reference.

The compositions of the described invention may be in the form of suppositories for rectal administration of the composition. "Rectal" or "rectally" as used herein refers to introduction into the body through the rectum where absorption occurs through the walls of the rectum. These compositions can be prepared by mixing the drug with a suitable nonirritating excipient such as cocoa butter and polyethylene glycols which are solid at ordinary temperatures but liquid at the rectal temperature and will therefore melt in the rectum and release the drug. When formulated as a suppository the compositions of the invention may be formulated with traditional binders and carriers, such as triglycerides.

The methods of these embodiments are clinically useful for treating all types of wounds to reduce adhesion formation, both for reducing initial adhesion formation, and for therapeutic treatment of existing adhesions. To treat existing adhesions, the method comprises the steps of excising the adhesion scar after its formation, treating the excision site with the composition of the invention, and allowing the excision site to heal more slowly.

In some embodiments, individuals in need of therapy for treating or limiting fibrotic disorders are those suffering from or at risk of one or more fibrotic disorders associated with TGFβ-induced connective tissue growth factor ("CTGF") expression, including but not limited to tissue fibrosis (including but not limited to idiopathic pulmonary fibrosis, hepatic fibrosis, renal fibrosis, retroperitoneal fibrosis, cystic fibrosis, blood vessel fibrosis, CNS fibrosis, and heart tissue fibrosis); diabetic nephropathy, glomerulosclerosis, and IgA nephropathy (causes of kidney failure and the need for dialysis and retransplant); diabetic retinopathy and macular degeneration (fibrotic diseases of the eye and leading causes of blindness); cirrhosis and biliary atresia (leading causes of liver fibrosis and failure); congestive heart failure; lung fibrosis; scleroderma; abdominal adhesions; and interstitial fibrosis. CTGF is a cysteine-rich, matrix-associated, heparin-binding protein. CTGF has a role in extracellular matrix remodeling in wound healing, scleroderma and other fibrotic processes, as it is capable of upregulating both matrix metalloproteinases (MMPs) and their inhibitors (TIMPs).

In various other embodiments, individuals in need of therapy for treating and/or limiting fibrotic disorders are those with elevated levels of one or more of the following biomarkers: TGFβ1 expression; Collagen I; CTGF expression; and alpha smooth muscle actin.

Transforming growth factor beta (TGFβ1) is a polypeptide member of the transforming growth factor beta superfamily of the cytokines. It is a secreted protein that performs many cellular functions, including the control of cell growth, cell proliferation, cell differentiation, and apoptosis.

Type-I collagen is the most abundant collagen of the human body. It is present in scar tissue. It also is found in tendons, the endomysium of myofibrils and the organic part of bone. The major component of Type-I collagen is encoded by the gene COL1A1.

Alpha-smooth muscle (alpha-sm) actin is an isoform typical of smooth muscle cells (SMC) and is present in high amounts in vascular SMC. Alpha-sm is utilized as a differentiation marker of SMCs.

Elevated levels of such biomarkers can be detected using standard techniques, including but not limited to immunological techniques (ELISA, immunocytochemistry, etc.) using commercially available antibodies against the one or more biomarkers As disclosed below, the polypeptides of the invention inhibit TGFβ1-induced CTGF and collagen expression in human keloid fibroblasts, which are elevated in fibrotic conditions, indicating that individuals with elevated levels of one or more of these biomarkers may especially benefit from the methods of the described invention. As used herein, an "elevated" level of the one or more biomarkers means any increase above normal for that individual or similarly situated individuals in a relevant target tissue. Such target tissues are those affected by fibrotic conditions, including but not limited to blood, wound exudate, and biopsies taken from tissues affected by fibrosis including but not limited to those disclosed above (skin, kidney, lung, liver, peritoneum, blood vessel, heart, retina, etc.) In various further embodiments, an individual in need thereof is one that has a level of one or more of the recited biomarkers 5%, 10%, 15%, 20%, 25%, 50%, 75%, 100%, or more above normal levels. Determining the level of the one or more biomarkers can be done using standard techniques in the art for measuring protein and/or gene expression, including but not limited to those disclosed below.

A "normal" level of these one or more biomarkers may be established by any suitable means, including but not limited to determining a normal level in that individual or similarly situated individuals in the absence of fibrotic conditions and/or keloids, or any other suitable means to establish a standard for reference. A method to treat a disease, disorder or condition according to the described invention comprises the steps of (1) administering to a subject in need thereof a therapeutically effective amount of a composition according to the described invention; (2) monitoring a level of at least one biomarker in a target tissue, wherein the at least one biomarker is selected from the group consisting of: TGFβ1 expression; collagen I expression; CTGF expression; and α-smooth muscle actin expression; and (3) maintaining the level of the biomarker in the target tissue substantially at normal levels during treatment.

In other embodiments, the methods of the invention are used to treat or limit the incidence of inflammation.

In various other embodiments, individuals in need of therapy for treating and/or limiting inflammatory disorders and/or autoimmune diseases oftentimes are those with elevated levels of one or more of the following biomarkers: TGFβ1 expression; TNF-α; IL-1; IL-6; IL-8; COX-2; MIP-1α; and MIP-2.

Tumor necrosis factor alpha (TNF-α) is a cytokine involved in systemic inflammation and is a member of a group of cytokines that all stimulate the acute phase reaction. TNF causes apoptotic cell death; cellular proliferation, differentiation, inflammation, tumorigenesis and viral replication.

Interleukin-1 (IL-1) is a cytokine composed of IL-1α and IL-1β. Both IL-1α and IL-1β are produced by macrophages, monocytes and dendritic cells. They form an important part of the inflammatory response of the body against infection. These cytokines increase the expression of adhesion factors on endothelial cells to enable transmigration of leukocytes to sites of infection and re-set the hypothalamus thermoregulatory center, leading to an increased body temperature which expresses itself as fever.

Interleukin-6 (IL-6) is an interleukin that acts as both a pro-inflammatory and anti-inflammatory cytokine. It is secreted by T cells and macrophages to stimulate immune response to trauma, especially burns or other tissue damage leading to inflammation.

Interleukin-8 (IL-8) is a chemokine produced by macrophages and other cell types such as epithelial cells. It is also synthesized by endothelial cells, which store IL-8 in their storage vesicles, the Weibel-Palade bodies. Primary function of IL-8 is the induction of chemotaxis in its target cells (e.g. neutrophil granulocytes).

Cyclooxygenase (COX) is an enzyme (EC 1.14.99.1) that is responsible for formation of important biological mediators called prostanoids (including prostaglandins, prostacyclin and thromboxane). COX-1 and COX-2 are of similar molecular weight (approximately 70 and 72 kDa respectively), and having 65% amino acid sequence homology and near-identical catalytic sites. The most significant difference between the isoenzymes, which allows for selective inhibition, is the substitution of isoleucine at position 523 in COX-1 with valine in COX-2. The relatively smaller Val523 residue in COX-2 allows access to a hydrophobic side-pocket in the enzyme (which Ile523 sterically hinders).

Macrophage Inflammatory Proteins (MIP) belong to the family of chemotactic cytokines known as chemokines. MIPs activate human granulocytes (neutrophils, eosinophils and basophils) which can lead to acute neutrophilic inflammation. They also induce the synthesis and release of other pro-inflammatory cytokines such as interleukin 1 (IL-1), IL-6 and TNF-α from fibroblasts and macrophages. Macrophage inflammatory protein-1 (MIP-1) is a monokine that is involved in the acute inflammatory state in the recruitment and activation of polymorphonuclear leukocytes.

Elevated levels of such biomarkers may be detected using standard techniques, including but not limited to immunological techniques (ELISA, immunocytochemistry, etc.) using commercially available antibodies against the one or more biomarkers.

Symptoms characteristic of inflammation (for which the methods of the invention can be used to treat or reduce incidence of) include, but are not limited to redness, heat, swelling, pain, and dysfunction of the organs involved. Specific inflammatory disorders that can be treated, or whose incidence can be reduced, by the methods of the invention include, but are not limited to, asthma, arthritis (rheumatoid or degenerative), sepsis, endotoxemic shock, psoriasis, radiation enteritis, scleroderma, cirrhosis, interstitial fibrosis, Crohn's disease, inflammatory bowel disease, appendicitis, gastritis, laryngitis, meningitis, pancreatitis, and otitis.

Without being limited by theory, it is believed that administration of the polypeptides of the invention to a patient in need of anti-inflammatory treatment suppresses the response to and/or expression of inflammatory cytokines including but not limited to TGF β1, tumor necrosis factor α (TNF-α), interleukin 1 (IL-1), IL-6, IL-8, COX-2, and macrophage inflammatory protein (e.g., MIP-1α and MIP-2).

In all of the above embodiments of the therapeutic methods of the invention, the polypeptides of the invention may be used as the sole active agent, or may be combined with one or more other treatments for the indication, as determined by an attending physician.

As used herein for all of the methods of the invention, a "therapeutically effective amount" or an "amount effective" of the one or more polypeptides is an amount that is sufficient to provide the intended benefit of treatment. An effective amount of the polypeptides that can be employed ranges generally between about 0.01 µg/kg body weight and about 10 mg/kg body weight, preferably ranging between about 0.05 µg/kg and about 5 mg/kg body weight. However dosage levels are based on a variety of factors, including the type of injury, the age, weight, sex, medical condition of the individual, the severity of the condition, the route of administration, and the particular compound employed. Thus, the dosage regimen may vary widely, but can be determined routinely by a physician using standard methods.

The term "abdominal adhesion preventing amount" of a polypeptide refers to an amount that is sufficient to inhibit, circumvent, prohibit, or reduce the formation, occurrence, or risk of formation or occurrence of an abdominal adhesion in a subject.

The term "disposed" as used herein refers to place or put in or on in a sequential, nonsequential, random, nonrandom, uniform, or nonuniform order, density, thickness, concentration, or volume.

The term "matrix" as used herein refers to a substance within which something else originates, develops, or is contained.

Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, Calif.), *Culture of Animal Cells: A Manual of Basic Technique, 2nd Ed.* (R. I. Freshney. 1987. Liss, Inc. New York, N.Y.), and *Gene Transfer and Expression Protocols*, pp. 109-128, ed. E. J. Murray, The Humana Press Inc., Clifton, N.J.), all of which are incorporated herein by reference.

As used herein, the singular forms "a", "an" and "the" include plural referents unless the context clearly dictates otherwise. For example, reference to a "polypeptide" means one or more polypeptides.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and described the methods and/or materials in connection with which the publications are cited.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Intestinal Adhesion Model

Experiments in an animal intestinal adhesion model of human disease will be used to determine the effect of the polypeptide having the sequence SEQ ID NO: 1. These animal models have been used by other investigators, and are generally accepted as such. The therapeutic results obtained with this model therefore may be extrapolated to methods of treating human subjects.

Animal studies will be carried out in the AAALAC accredited animal facilities at Purdue University in accordance with the National Institutes of Health Guide for Care and Use of Animals. Male Sprague-Dawley rat weighing between 240-280 g will be included in the study. The cohorts have been designed to include a positive control, cecum abrasion, no treatment, and a negative control, no abrasion, no treatment, as well as additional cohorts to evaluate the optimal delivery method to prevent intestinal adhesions. All animals will be maintained in separate cages under a 12 hour light/dark cycle and provided food and water ad libitum both before and following surgery. All animals will be anesthetized using an intra peritoneal injection of ketamine (75-100 mg/kg) and xylazine (5-10 mg/kg). Anesthesia will be maintained with an intra peritoneal injection of 10% induction dose of ketamine/xylazine. Anesthetic levels will be assessed using the toe pinch method. Also, the animal's respiration and color of mucous membrane will be monitored during the procedure. Animals will be euthanized using barbiturate overdose (e.g., Nembutal 120 mg/kg) or similar commercially available euthanasia solution at the recommended dosage IV or IP.

Anesthetized rats will be prepped for surgery by shaving the lower abdomen and cleaning it with iodine. Animals will undergo a midline celiotomy, the cecum will be identified and placed onto a gauze pad and saline used to keep the tissue moist. The cecum wall will be abraded using 1×1 cm electrosurgical tip cleaner, Johnson and Johnson, until bleeding is noted on the anterior surface. A 1.6 mm×0.8 mm defect will be created in the peritoneum and underlying muscle using a 0.8 mm biopsy punch. The abdominal cavity will be irrigated prior to application of treatments. The appropriate treatment will be applied between the juxtaposed cecum and injured peritoneum. Specifically, in cohort 1 the abraded cecum will be juxtaposed to the injured peritoneum and the surgical incision closed. Cohort 2 will be subjected to only the celiotomy and the incision will be closed. Additional cohorts will be irrigated with 10 mls of PBS containing the appropriate concentration, of MK2 inhibitor. If injury such as a perforated bowel occurs during surgery or the barrier fails to separate the damaged tissue, the animal will be removed from the study and replaced [Buckenmaier, C. C., 3rd, et al., Comparison of antiadhesive treatments using an objective rat model. Am Surg, 1999. 65(3): p. 274-82; Zong, X., et al., Prevention of postsurgery-induced abdominal adhesions by electrospun bioabsorbable nanofibrous poly(lactide-co-glycolide)-based membranes. Ann Surg, 2004. 240(5): p. 910-5].

Fourteen days post-surgery the rats will again be anesthetized as described above and a surgeon who is blinded to the treatments will perform a second celiotomy to evaluate the extent and severity of the adhesions. The vast majority of abdominal adhesion studies use a visual analogue scoring system rather than histology. The following scoring system will be used: 0=no adhesions, 1=thin and filmy, easily separated adhesions, 2=significant and filmy, difficult to separate tissue and 3=severe with fibrosis, instruments required to separate tissue. The number of animals within each group with adhesions and the severity of adhesions will be noted and then compared across groups using ANOVA analysis to determine the best treatment combination (barrier, rate of release and drug concentration) to inhibit adhesions.

Example 2

Efficacy Of Peptide YARAAARQARAKALARQLGVAA [SEQ ID NO: 1] in Adhesion Prevention and Its Effect on Bowel Anastomosis Experiments in an animal intestinal adhesion model of human disease have been used to determine the efficacy of a polypeptide having the amino acid sequence SEQ ID NO: 1 in adhesion prevention and on bowel anastomosis. Because this animal model has been used by other investigators, and is generally accepted as such, the therapeutic results obtained with this model may be extrapolated to methods of treating human subjects.

Forty (40) male Sprague Dawley rats were individually caged and allowed a 5 day acclimatization period. All animals were offered food and water ad lib, using standard pelleted lab chow. All animals were pre-treated with Buprenophrine (50 µg/kg) injected subcutaneously preoperatively a half hour before surgery for pain control. Anesthesia was achieved by using Ketamine (35 mg/kg) IM into the right hind leg and Xylazine (5 mg/kg) IM into the left hind leg.

After adequate anesthetic levels were achieved, the abdomen was clipped free of hair and prepped with Betadine solution. A 3 cm vertical midline abdominal incision was made using a 15 blade. The small bowel was retracted superiorly and the descending colon was exposed. The sigmoid colon was divided sharply approximately 2 cm superior to the peritoneal reflection. Using 6-0 Prolene, 8 interrupted sutures were placed to create a hand sewn anastomosis.

Any areas with visible gaps also had additional stitches placed.

Prior to closure, 5 ml of test solution (peptide drug dissolved in sterile normal saline, final concentration 100 µM) or saline were placed over the anastomosis and into the abdominal cavity and pelvis. The abdomen was then closed in a running, continuous fashion with a 3-0 silk suture, and the skin was closed in the same fashion as a separate layer. The animals were placed in a recovery area under Gaymar heating pumps until fully awake from anesthesia. Buprenorphrine was further injected 4 hours after surgery as well as the next morning for pain control.

Sacrifice was carried out 4 and 10 days from the date of surgery (10 animals, 5 from each group were operated each day). The sacrifice points were chosen deliberately because at 4 days the effect on bowel integrity, if it exists, would be expected to be most prominent; and 2) ten day time frame is one of maximal adhesion formation.

The animals were euthanized with Euthasol (200 mg/kg). The abdominal cavity was entered using a left lateral paramedian incision; then two horizontal incisions were made at the apices of the incision so that a flap could be pulled back and adhesion formation to the anterior abdominal wall could be evaluated without inadvertently harming any tissue.

The anastomosis then was identified after carefully retracting any overlying non-adherent viscera. Any adhesion formation directly to the anastomosis was kept in place with no attempt to remove or disturb this area. Pictures were taken of the anastomosis for further evaluation. This is the second part of the adhesion scoring system. A "1" was assigned for each tissue found to be adherent to the anastomosis, including epididymal fat, omentum, small bowel, large bowel. All of the possibilities were added as part of a cumulative score.

Colonic bursting pressure was then measured. Using a silk tie, the colon distal to the anastomosis was milked free of stool and ligated. The remainder of any colonic contents was carefully milked proximally and then the colon was sharply divided proximal to the anastomosis. An 18 gauge angiocath was inserted into the colonic lumen and again a silk tie was used to tie off the proximal end and included the angiocath to secure it in place and assure no leakage. The angiocath was connected to a pressure transducer, and an infusion pump was preset to deliver 300 cc/hr of normal saline as a means of increasing gradually the intra-colonic pressure. The point at which the colon began to leak saline or the pressure dropped suddenly was recorded as the bursting pressure, regardless of whether the leak occurred at the anastomosis or outside the suture line.

Next the adhesions to the anastomosis were graded for density and tenacity. The adhesions were teased or dissected from the anastomosis and graded according to difficulty in dissection. This score was included as part of the cumulative total.

The anastomosis then was excised with a 5 mm margin on either side. Part was stored at −20° C. for hydroxyproline analysis, as an index of collagen content. The other segment of the anastosmosis was placed in RNAlater for possible Northern analysis at a subsequent time.

TABLE 1

Adhesion scoring system:

| | Score |
|---|---|
| Adhesion Location | |
| Adhesions to abd wall | 1 |
| Epid. Fat to anast. | 1 |
| Sm. Bowel to anast. | 1 |
| Colon to anast. | 1 |
| Omentum to anast | 1 |
| Density | |
| Light, flimsy, easily dissected | 1 |
| Moderate, adherent, some force needed | 2 |
| Heavy, needs sharp dissection | 3 |

Theoretically, the smallest possible score is 0, the highest possible score is 8.

The animals lose a significant amount of body weight during the first 48-72 hrs but then regain it. There was one anesthetic death in the peptide group in the 4 day group. In the 10 day group, there were two deaths postoperatively in the control group, one from a transverse colonic volvulus 5 days after surgery and one from an anastomotic leak 7 days after surgery; there was one death in the peptide group on postoperative day 6, but autopsy revealed no obvious cause. Overall mortality for these two experiments was therefore 10%.

As shown in Table 2 there is some weight loss initially in the peptide treated group, however, by day ten, the weight loss is not significant and is in fact less than seen in the control group. Normal collagen synthesis was determined by measuring the hydroxyproline content (OHP, used to determine collagen content) within oxidation products from tissue at the anastomosis site. No inhibition in normal healing was seen based on the OHP content and burst strength. The adhesion scores demonstrate a significant reduction in number and severity of the adhesions formed at day 10.

TABLE 2

Summary of Data - Mean ± SEM

| | Weight gain (Cumulative) | Bursting pressure (mmHg) | OHP anastomosis | Adhesion Organ Score | Adhesion Severity Score | Adhesion Cumulative Score |
|---|---|---|---|---|---|---|
| Control 4 days | 0.7 ± 4.3 | 96 ± 32 | 2679 ± 475 | 2.2 ± 0.2 | 2.4 ± 0.2 | 4.7 ± 0.4 |
| Peptide 4 days | −3.3 ± 5.2 | 86 ± 13 | 2055 ± 184 | 2.0 ± 0.2 | 2.1 ± 0.2 | 4.1 ± 0.3 |
| P | NS | NS | NS | NS | NS | NS |
| Control 10 days | −5.6 ± 3.1 | 191 ± 29 | 4980 ± 205 | 3.4 ± 0.3 | 2.6 ± 0.2 | 6.0 ± 0.3 |
| Peptide 10 days | −1.3 ± 3.7 | 175 ± 27 | 5284 ± 218 | 2.1 ± 0.2 | 1.5 ± 0.3 | 3.8 ± 0.4 |
| P | NS | NS | NS | 0.003 | 0.023 | 0.00296 ± 32 |

Oxidized hydroxyproline (OHP) from the anastamosis sight is used to measure new collagen synthesis to confirm the drug is not impairing normal healing.

As used in Table 2, "bursting pressure" refers to the minimum internal pressure that will cause the colon rupture or split open The peptide decreased significantly both the number and the quality of adhesions at day 10 (most relevant time point)

without affecting bowel bursting pressure or OHP content at day 4 (most relevant) or day 10.

While the present invention has been described with reference to the specific embodiments thereof it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the present invention. All such modifications are intended to be within the scope of the claims appended hereto.

What is claimed is:

1. A pharmaceutical composition to reduce incidence or extent of a scar tissue binding together two anatomic surfaces normally separated from each other that develops after surgery, inflammation or injury in a subject in need thereof, the composition comprising a therapeutic amount of a polypeptide consisting of amino acid sequence YARAAARQARAKALARQLGVAA [SEQ ID NO: 1] and a pharmaceutically acceptable carrier, the composition being characterized by a therapeutic effect of the therapeutic amount to reduce incidence, severity, or both, of the scar tissue without impairing normal healing.

2. The composition according to claim 1, wherein the scar tissue is abdominal scar tissue binding together two anatomical surfaces normally separated from each other that develops after surgery, inflammation or injury.

3. The composition according to claim 1, wherein the scar tissue is pelvic scar tissue binding together two anatomical surfaces normally separated from each other that develops after surgery, inflammation or injury.

4. The composition according to claim 1, wherein the scar tissue is cardiac scar tissue binding together two anatomical surfaces normally separated from each other that develops after surgery, inflammation or injury.

5. The composition according to claim 1, wherein the composition is formulated to be applied topically.

6. The composition according to claim 5, wherein the composition is disposed on or in a biomedical device.

7. The composition according to claim 1, wherein the composition is formulated to be applied parenterally.

8. The composition according to claim 7, wherein the composition is disposed on or in a biomedical device.

9. A biomedical device for reducing incidence or extent of a scar tissue binding together two anatomic surfaces normally separated from each other that develops after surgery, inflammation or injury, the device comprising a pharmaceutical composition containing a therapeutic amount of a polypeptide consisting of amino acid sequence YARAAARQARAKALARQLGVAA [SEQ ID NO: 1] disposed on or in the device, the device being characterized by a therapeutic effect of the therapeutic amount to reduce incidence, severity, or both, of the scar tissue without impairing normal healing.

10. The biomedical device according to claim 9, wherein the scar tissue binding together two anatomical surfaces normally separated from each other that develops after surgery, inflammation or injury is abdominal scar tissue.

11. The biomedical device according to claim 9, wherein the scar tissue binding together two anatomical surfaces normally separated from each other that develops after surgery, inflammation or injury is pelvic scar tissue.

12. The biomedical device according to claim 9, wherein the scar tissue binding together two anatomical surfaces normally separated from each other that develops after surgery, inflammation or injury is cardiac scar tissue.

13. The biomedical device according to claim 9, wherein the polypeptide is disposed in a matrix disposed on the device.

14. The biomedical device according to claim 13, wherein the matrix is a heparin coating.

15. A method for reducing incidence or extent of a scar tissue binding together two anatomic surfaces normally separated from each other that develops after surgery, inflammation or injury in a subject in need thereof, the method comprising the step of (a) administering before scar formation a therapeutic amount of a composition comprising a therapeutic amount of a polypeptide consisting of amino acid sequence YARAAARQARAKALARQLGVAA [SEQ ID NO: 1] and a pharmaceutically acceptable carrier to at least one anatomic surface at risk for developing a scar tissue binding together two anatomic surfaces normally separated from each other or to a scar tissue binding together two anatomic surfaces normally separated from each other, wherein the therapeutic amount is effective to reduce incidence, severity, or both, of the scar tissue without impairing normal healing.

16. The method according to claim 15, wherein the scar tissue is at least one selected from the group consisting of an abdominal scar tissue, a pelvic scar tissue, a cardiac scar tissue, a small intestine scar tissue, and a large intestine scar tissue, and wherein the scar tissue results from surgical intervention.

17. The method according to claim 15, wherein the scar tissue is abdominal scar tissue binding together two anatomical surfaces normally separated from each other that develops after surgery, inflammation or injury.

18. The method according to claim 15, wherein the scar tissue is pelvic scar tissue binding together two anatomical surfaces normally separated from each other that develops after surgery, inflammation or injury.

19. The method according to claim 15, wherein the scar tissue is cardiac scar tissue binding together two anatomical surfaces normally separated from each other that develops after surgery, inflammation or injury.

20. The method according to claim 15, wherein the scar tissue is small intestine scar tissue binding together two anatomical surfaces normally separated from each other that develops after surgery, inflammation or injury.

21. The method according to claim 15, wherein the scar tissue is large intestine scar tissue binding together two anatomical surfaces normally separated from each other that develops after surgery, inflammation or injury.

22. The method according to claim 15, wherein the scar tissue is existing scar tissue binding together two anatomical surfaces normally separated from each other that develops after surgery, inflammation or injury.

23. The method according to claim 15, wherein the method is effective to reduce inflammation comprising an inflammatory cytokine selected from the group consisting of transforming growth factor β1 (TGF β1), tumor necrosis factor α (TNF-α), interleukin 1 (IL-1), interleukin 6 (IL-6), interleukin 8 (IL-8), cyclooxygenase-2 (COX-2), macrophage inflammatory protein-1α (MIP-1α), macrophage inflammatory protein-2 (MIP-2) and a combination thereof, in proximity to the anatomic surface at risk for developing the scar tissue, and the anatomic surface at risk for developing the scar tissue is selected from the group consisting of abdominal tissue, pelvic tissue, and cardiac tissue.

24. The method according to claim 23, further comprising (b) monitoring a level of at least one biomarker in the target tissue, wherein the level of the at least one biomarker in the target tissue in proximity to the scar tissue is elevated when compared to a normal level of the at least one biomarker in the target tissue, wherein the at least one biomarker is selected from the group consisting of: transforming growth factor beta 1 (TGFβ1); collagen I; connective tissue growth factor (CTGF); α-smooth muscle actin; tumor necrosis factor alpha (TNF-α); interleukin 1 (IL-1); interleukin 6 (IL-6); interleukin 8 (IL-8); cyclooxygenase 2 (COX-2); and a macrophage inflammatory protein (MIP).

25. The method according to claim 22, wherein the existing scar tissue is at least one selected from the group consisting of an existing abdominal scar tissue, an existing pelvic scar tissue, an existing cardiac scar tissue, an existing small intestine scar tissue, an existing large intestine scar tissue, and wherein the existing scar tissue results from surgical intervention.

26. The method according to claim 22, wherein the existing scar tissue is an existing abdominal scar tissue.

27. The method according to claim 22, wherein the existing scar tissue is an existing pelvic scar tissue.

28. The method according to claim 22, wherein the existing scar tissue is an existing cardiac scar tissue.

29. The method according to claim 22, wherein the existing scar tissue is an existing small intestine scar tissue.

30. The method according to claim 22, wherein the existing scar tissue is an existing large intestine scar tissue.

31. The method according to claim 22, wherein administering step (a) further comprises:
(i) surgically excising the existing scar tissue, thereby creating an excision site;
(ii) reconnecting excised surfaces of the excision site;
(iii) treating the excision site with the composition comprising the therapeutic amount of the polypeptide consisting of amino acid sequence YARAAARQARAKALARQLGVAA [SEQ ID NO: 1] and the pharmaceutically acceptable carrier; and
(iv) allowing the excision site to heal in the presence of the composition without impairing normal healing.

32. The method according to claim 24, further comprising the steps of:
(b) monitoring the level of the at least one biomarker in the target tissue affected by the scar tissue; and
(c) maintaining the level of the at least one biomarker in the target tissue affected by the scar tissue substantially at the normal level.

\* \* \* \* \*

SEQUENCE LISTING

<160> NUMBER OF SEQ ID NOS: 1

<210> SEQ ID NO 1
<211> LENGTH: 22
<212> TYPE: PRT
<213> ORGANISM: Unknown
<220> FEATURE:
<223> OTHER INFORMATION: MAMMALIAN

<400> SEQUENCE: 1

Tyr Ala Arg Ala Ala Ala Arg Gln Ala Arg Ala Lys Ala Leu Ala Arg
1               5                   10                  15

Gln Leu Gly Val Ala Ala
            20